(12) United States Patent
Wisniewski et al.

(10) Patent No.: US 6,453,683 B1
(45) Date of Patent: Sep. 24, 2002

(54) TAPERED SLOT CRYOPRESERVATION SYSTEM WITH CONTROLLED DENDRITIC FREEZING FRONT VELOCITY

(75) Inventors: Richard Wisniewski, San Mateo, CA (US); Eric Lee, Acton, MA (US)

(73) Assignee: Integrated Biosystems, Inc., Napa, CA (US)

( * ) Notice: Subject to any disclaimer, the term of this patent is extended or adjusted under 35 U.S.C. 154(b) by 0 days.

(21) Appl. No.: 09/905,488

(22) Filed: Jul. 13, 2001

Related U.S. Application Data (63) Continuation-in-part of application No. 09/863,126, filed on May 22, 2001.

(51) Int. Cl.[7] .............................. F25C 1/00; A23G 9/00
(52) U.S. Cl. ............................................. 62/75; 62/135
(58) Field of Search .............................. 62/66, 75, 135, 62/340

(56) References Cited

U.S. PATENT DOCUMENTS

| | | | | |
|---|---|---|---|---|
| 2,662,520 A | * | 12/1953 | McMahon | 435/1.3 |
| 3,121,627 A | * | 2/1964 | Harris, Sr. | 62/124 |
| 3,959,981 A | * | 6/1976 | Anderson | 62/135 |
| 4,986,080 A | * | 1/1991 | Grigoli et al. | 425/126.2 |
| 5,374,436 A | * | 12/1994 | White et al. | 426/249 |
| 5,582,856 A | * | 12/1996 | White et al. | 426/249 |
| 6,220,038 B1 | * | 4/2001 | Marsh et al. | 62/353 |

* cited by examiner

Primary Examiner—William E. Tapolcai
(74) Attorney, Agent, or Firm—Heslin Rothenberg Farley & Mesiti P.C.

(57) ABSTRACT

A biopharmaceutical material cryopreservation system, including a flexible sterile container comprising a biocompatible polymeric material, and the flexible sterile container containing biopharmaceuticals materials, and a freezing system removably coupled to the flexible sterile container via a tapered slot and the freezing system thermally coupled to the biopharmaceutical materials via the flexible sterile container and the tapered slot; wherein the freezing system comprises a feedback loop constructed to control a dendrite freezing front velocity, within the biopharmaceutical materials, in a range from approximately 5 millimeters per hour to approximately 250 millimeters per hour based on feedback information from the temperature sensor. Also disclosed are methods of cryopreservation of biopharmaceutical materials, and methods of linearly scaling processes for cryopreservation of biopharmaceutical materials.

28 Claims, 3 Drawing Sheets

TAPERED SLOT CRYOPRESERVATION SYSTEM WITH CONTROLLED DENDRITIC FREEZING FRONT VELOCITY

CROSS REFERENCE TO RELATED APPLICATIONS

This application is a continuation-in-part of U.S. Pat. application Ser. No. 09/863,126, filed on May 22, 2001.

BACKGROUND OF THE INVENTION

1. Field of the Invention

This invention relates to biopharmaceutical material cryogenic preservation methods and apparatus, and more particularly to a biopharmaceutical material cryogenic preservation system and method which maintains a controlled dendritic freezing front velocity.

2. Description of Related Art

Cryopreservation of biopharmaceutical materials is important in the manufacturing, use, storage and sale of such materials. For example, biopharmaceutical materials are often cryopreserved by freezing between processing steps and during storage. Similarly, in certain cases, biopharmaceutical materials are frozen and thawed as part of the development process to enhance their quality or to simplify the development process.

When utilizing cryopreservation, the overall quality, and in particular pharmaceutical activity, of the pharmaceutical materials is desirably preserved, without substantial degradation of the biopharmaceutical materials.

Currently, in some aspects, cryopreservation of biopharmaceutical materials involves placing a container comprising the biopharmaceutical materials in a cabinet or chest freezer and allowing the biopharmaceutical materials to freeze. In current cryopreservation techniques, a container enclosing biopharmaceutical materials is placed on a solid or wire-frame shelf in the cabinet or chest freezer. The biopharmaceutical materials are left to freeze until they are solid, in an uncontrolled fashion.

Significant losses in biopharmaceutical material activity have been noted using such current techniques. For example, observers have noted that stability and conformation of biopharmaceutical materials can be affected by low temperature alone, without any significant changes in variables such as solute concentration or pH.

Further, it has been noted that conventional cryopreservation methods can lead to cryoconcentration, or the redistribution of solutes from the frozen volume to the unfrozen cavity where their concentration may significantly increase. The result of cryoconcentration can include the crystallization of buffer components leading to a pH change that can affect stability, folding, or even create cleavage of the biopharmaceutical material. Cryoconcentration in conjunction with low temperature effects may cause a decrease in solubility of the biopharmaceutical material, with resulting precipitation. Product aggregation (i.e. increase in molecular weight) has also been observed.

Additionally, damage to the containers has been noted using conventional cryopreservation techniques. Container damage may be caused by freezing stress due to volumetric expansion of aqueous biopharmaceutical materials during freezing. Rupture or damage to the integrity of the container is undesirable, as it can compromise sterility or lead to biopharmaceutical material contamination or leakage or loss of the biopharmaceutical material.

Another problem faced by those of skill in the art is that currently available process methods and apparatus designs intended for cryopreservation of biopharmaceutical materials generally do not exhibit good linear scalability. In biopharmaceutical manufacturing, there is a constant need for simple, efficient and predictable scale-up. Methods developed at research and pilot stages should be directly scalable to the production scale without compromising biopharmaceutical material quality (e.g. biological activity of the biopharmaceutical material) or process productivity. The predictability of process behavior based on information developed on a small scale is often referred to as linear scalability.

In scaling up a cryopreservation process, discrete containers such as bottles, carboys, tanks, or similar single containers are available in different sizes. In virtually all cases, the rate of completely freezing the biopharmaceutical materials in each vessel is related to the largest distance from the cooling surface. Consequently, longer times are required to freeze the contents of larger containers if the same cooling surface temperature is maintained. Such longer times are undersirable because this results in lower process throughputs. Additionally, increases in the freezing volume may have an unpredictable impact on biopharmaceutical material activities in certain cases.

Various strategies have been adopted to mitigate this scale up problem. To freeze large quantities, one could for example use multiple smaller containers. However, adjacent placement of multiple containers in a freezer creates thermal gradients from container to container. The freezing rate and product quality depend on the actual freezer load, spacing between the containers, and air movement in the freezer. The result is different thermal history for the contents of individual containers. For a large batch, it is also time consuming and counter-productive to divide the lot into a large number of subunits. Product loss is likely to be important as it is, to some extent, proportional to the container surface and to the number of containers.

Accordingly, there is a need for apparatus and methods for cryopreservation of biopharmaceutical materials that solve the deficiencies noted above.

SUMMARY OF THE INVENTION

In an aspect, the invention relates to a biopharmaceutical material cryopreservation system comprising a flexible sterile container comprising a biocompatible polymeric material, and the flexible sterile container containing biopharmaceuticals materials, and; a freezing system removably coupled to the flexible sterile container via a tapered slot and the freezing system thermally coupled to the biopharmaceutical materials via the flexible sterile container and the tapered slot; wherein the freezing system comprises a feedback loop constructed to control a dendritic freezing front velocity, within the biopharmaceutical materials, in a range from approximately 5 millimeters per hour to approximately 250 millimeters per hour based on feedback information from the temperature sensor.

In another aspect, the invention relates to a method for cryopreservation of biopharmaceutical materials, comprising providing a flexible sterile container comprising a biocompatible polymeric material, and the flexible sterile container containing biopharmaceuticals materials thermally coupling a freezing system to the biopharmaceutical materials via the flexible sterile container, and the freezing system comprising (i) a temperature sensor that monitors a temperature of the iopharmaceutical materials, and (ii) a feedback loop constructed to control a dendritic freezing front velocity; and controlling the dendritic freezing front velocity, within the biopharmaceutical materials, in a range from approximately 5 millimeters per hour to approximately 250 millimeters per hour based on feedback information from the temperature sensor.

In yet another aspect, the invention relates to a biopharmaceutical material cryopreservation system, comprising flexible sterile container means for counting biopharmaceutical products, and the flexible sterile container means comprising a biocompatible polymeric material, and the flexible sterile container containing biopharmaceuticals materials, and; freezing means for freezing the biopharmaceutical materials, and the freezing means thermally coupled to the biopharmaceutical materials via the flexible sterile container, and the freezing means comprising a temperature sensor that monitors a temperature of the biopharmaceutical materials wherein the freezing means comprises a feedback loop constructed to control a dendritic freezing front velocity, within the biopharmaceutical materials, in a range from approximately 5 millimeters per hour to approximately 250 millimeters per hour based on feedback information from the temperature sensor.

In still another aspect, the invention relates to a method of linearly scaling a process for cryopreserving a biopharmaceutical material comprising providing the biopharmaceutical material cryopreservation system of claim 1, wherein the biopharmaceutical material cryopreservation system possesses a first volume defined by a slab length, height, taper angle, and a first z dimension; determining a second volume; determining a second z dimension based on the values of the second volume, the slab length, the height, and the taper angle; and providing the biopharmaceutical material cryopreservation system, wherein the biopharmaceutical material cryopreservation system possesses the second volume defined by the slab length, the height, the taper angle, and the second z dimension.

DETAILED DESCRIPTION OF THE INVENTION

The inventor has unexpectedly discovered that controlling the freezing rate in cryopreservation and cryoprocessing of biopharmaceutical materials can solve the above-mentioned problems. According to an aspect of the present invention, the problems identified above may be partially or completely eliminated by ensuring that cryopreservation or cryoprocessing of biopharmaceutical materials is performed in a controlled manner such that the freezing rate of the biopharmaceutical materials is maintained within a desirable range.

When processing biopharmaceutical materials such as cells for cryopreservation, for example, if the cells are frozen too quickly, with too high of a water content, the cells may develop intracellular ice crystals. As a result, the cells may rupture and/or become unviable. On the other hand, if the cells are frozen too slowly, the cells are exposed to concentrated solutes over extended period of time, which may also lead to cell damage.

The freezing rate may affect biopharmaceutical material distribution within a frozen volume with nonuniform distribution of biopharmaceutical materials leading to detrimental effects. In an embodiment, control of the freezing rate may be represented as control of the dendritic freezing front velocity, with the dendritic freezing front moving from a cooled wall into a bulk region of the biopharmaceutical material. The freezing rate also affects the final frozen matrix, which may have biopharmaceutical material-protecting or biopharmaceutical material-damaging characteristics. For example, a frozen matrix with biopharmaceutical material embedded into a vitrified portion between dendritic ice crystals may be a biopharmaceutical material-protecting type. Biopharmaceutical material-damaging matrices may take different forms; for example: (1) a very tight cellular ice crystal matrix or (2) an assembly of a very large number of fine ice crystals with product located in very thin layers along the crystal boundaries. The frozen matrix characteristics depends on the ice crystal structure with preferred structure being the dendritic ice crystal structure. Such desirable matrix structure depends primarily on a freezing front velocity with other secondarily important factors being the temperature gradient, composition and concentration of solutes, and geometry of the freezing container.

According to the present invention, maintaining the velocity of a dendritic ice crystal freezing front (hereafter "dendritic freezing front") in a range from approximately 5 millimeters per hour to approximately 250 millimeters per hour, or more preferably in a range from approximately 8 millimeters per hour to approximately 180 millimeters per hour, or most preferably in a range from approximately 10 millimeters per hour to approximately 125 millimeters per hour, provides advantageous cryoprocessing conditions in a wide range of systems and feasible operating margins so that damage to biopharmaceutical materials may be minimized or avoided.

As an example, the following discussion illustrates the relationship between the velocity of dendritic freezing front and the size and spacing of frozen dendrites in the context of freezing of biopharmaceutical materials.

If the velocity of the dendritic freezing front is much lower than approximately 5 millimeters per hour, the dendrites are small and densely packed within the dendritic freezing front. Consequently, the dendritic freezing front behaves as a solid interface with solutes and biopharmaceutical materials not being integrated into the solid mass, but are being instead rejected and pushed towards the center of a flexible sterile container. This may result in damage to biopharmaceutical materials as previously discussed.

As the velocity of dendritic freezing front increases to, but still remains less than approximately 5 millimeters per hour, the dendrites grow somewhat larger in size and more separated, developing into cellular or columnar patterns. In this case, still only a small percentage of the solutes or biopharmaceutical materials become embedded into the solid mass. Instead, most of the solutes and biopharmaceutical materials are pushed forward by the advancing dendritic freezing front and their concentration in the liquid phase of biopharmaceutical material 110 increases. This situation may still result in damage to biopharmaceutical materials.

If the velocity of the dendritic freezing front is in a range from approximately 5 millimeters per hour to approximately 250 millimeters per hour, the dendrites grow sufficiently large and far apart to properly embed solutes and biopharmaceutical materials into the dendritic freezing front. One aspect of the present invention provides a method and apparatus for maintaining the velocity of dendritic freezing front in a range from approximately 5 millimeters per hour to approximately 250 millimeters per hour to provide proper conditions for successful cryopreservation and cryoprocessing of biopharmaceutical materials.

If the velocity of dendritic freezing front increases beyond approximately 250 millimeters per hour, dendrites start to decrease in size and become more compactly packed, thereby losing the ability to properly embed solutes and particles comprised in biopharmaceutical materials into freezing front.

If the velocity of dendritic freezing front is much higher than approximately 250 millimeters per hour, the resulting solid mass comprises a random, unequilibrated, structure of fine ice crystals. Such rapid cryocooling could be achieved, for example, by supercooling small volumes of biopharmaceutical materials, by freezing biopharmaceutical materials in thin layers, or by submerging small volumes of biopharmaceutical materials into liquid nitrogen or other cryogenic fluid.

For example, in biopharmaceutical materials subjected to supercooling in a liquid phase followed by a rapid ice crystal growth, the velocity of dendritic freezing front may exceed 1000 mm/sec. Such fast dendritic front velocities can create solid masses that comprise biopharmaceutical materials, wherein the solid masses are not formed of equilibrated ice crystals. These non-equilibrated solid masses are prone to ice recrystallization, when dissolution of smaller ice crystals and growth of larger ice crystals may impose excessive mechanical forces on biopharmaceutical materials. Further, biopharmaceutical materials in non-equilibrated solid masses may be distributed between ice crystals in very thin layers on grain boundaries. This produces a large product-ice contact interface area, due to the very large number of small ice crystals, which is detrimental to biopharmaceutical materials.

Inter-dendritic spacing can be regulated by increasing or decreasing the heat flux out of the system (thereby influencing thermal effects and the resulting dendritic freezing front velocities), and by selection and concentration of solutes.

The length of free dendrites may depend in part on the front velocity and on the temperature gradient along the dendrites. The free dendrite may refer to the length of the dendrite sticking into the liquid phase, or, alternatively, to the thickness of a "mushy zone", e.g. a mixture of dendritic ice crystal needles and liquid phase between them. At the tips of the dendrites, the temperature is close to 0 ° C., and decreases gradually to match the wall temperature along the dendrite length and the solidified mass away from the front. The temperature of liquid between the dendrites also decreases with nearness to the cold wall. As cryocooling continues, with certain solutes such as salts, the solute concentration reaches a eutectic concentration and temperature. The solution between the dendrites then solidifies, reaching the complete or substantially complete, or solid, dendritic state. This state is a matrix of the dendritic ice crystals and solidified solutes in a eutectic state between those dendritic ice crystals. Some solutes (for example carbohydrates) do not form eutectics. Instead they may form a glassy state or crystallize between the dendritic ice crystals. The glassy state may protect a biopharmaceutical product, whereas a crystalline state may have a detrimental effect upon a biopharmaceutical product. Dendritic ice crystals are described further in R. Wisniewski, *Developing Large-Scale Cryopreservation Systems for Biopharmaceutical Systems*, BioPharm 11(6):50–56 (1998) and R. Wisniewski, *Large Scale Cryopreservation of Cells. Cell Components, and Biological Solutions*, BioPharm 11(9):42–61 (1998), all of which are incorporated herein by reference.

Figure 1:
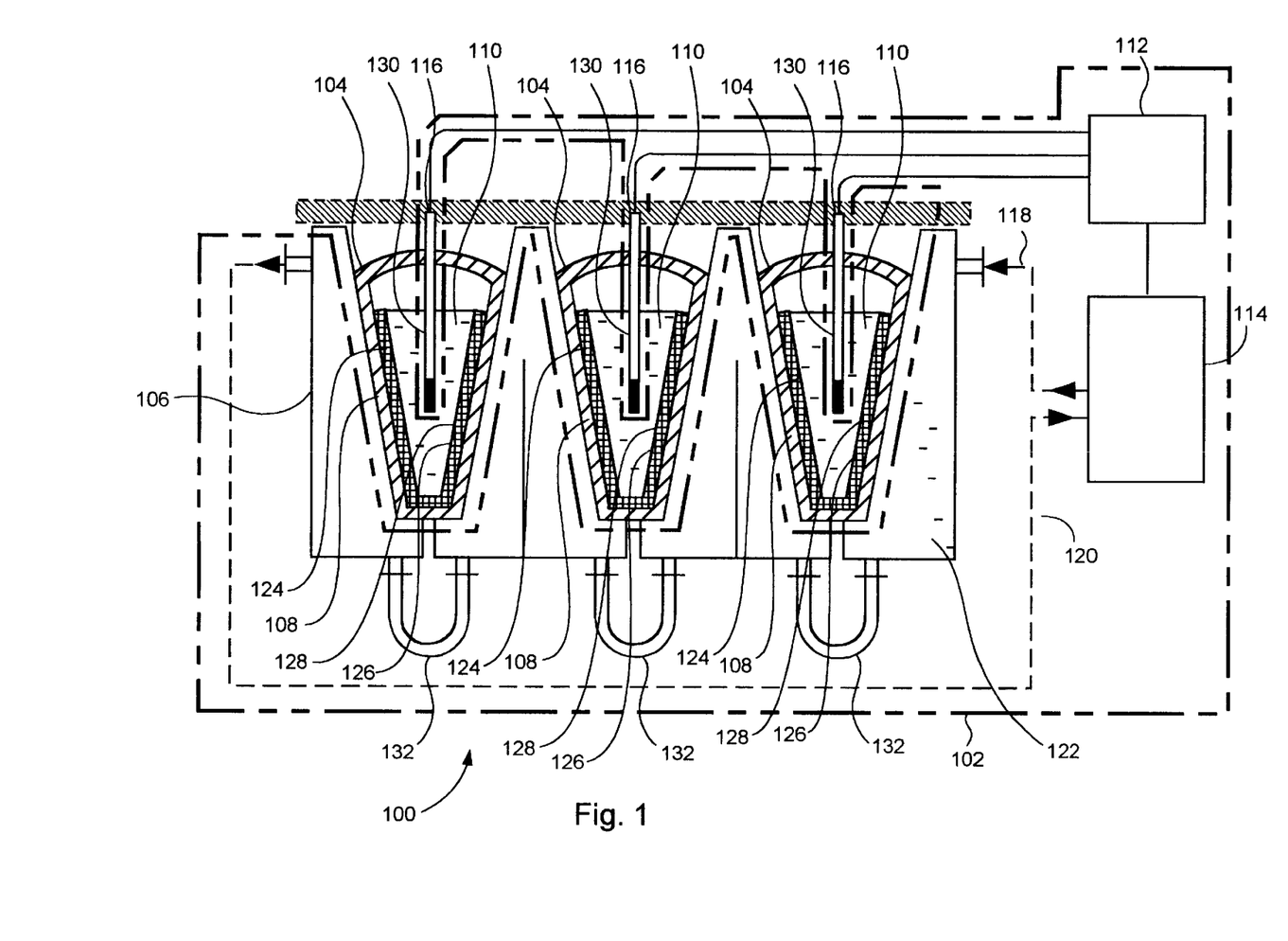
FIG. 1 shows a biopharmaceutical material cryopreservation system according to the present invention.

An inventive apparatus designed to utilize the above understandings is shown in FIG. 1, which shows a biopharmaceutical material cryopreservation system according to the present invention. Biopharmaceutical material cryopreservation system 100 comprises freezing system 102, flexible sterile container 104, cryocooling enclosure 106, temprature sensor port 108, biopharmaceutical materials 110, control system 112, cryorefrigeration system 114, temperature sensor 116, cryocoolant input flow 118, cryocoolant output flow 120, cryocoolant 122, solid mass 124, dendritic freezing front 126, dendrites 128, temperature sensor port 130, and hoses 132.

Structurally, flexible sterile container 104 is disposed within cryocooling enclosure 106, and within tapered slot 108. Three tapered slots 108 are shown in FIG. 1, but more tapered slots 108 or fewer slots 108 are within the scope of the invention. For instance, should it be desirable to increase the capacity of biopharmaceutical material cryopreservation system 100, additional tapered slots 108 could be added. As an example, a biopharmaceutical material cryopreservation system 100 with six tapered slots 108 would have roughly twice the capacity of the biopharmaceutical material cryopreservation system 100 shown in FIG. 1. If it were desired to reduce the capacity of biopharmaceutical material cryopreservation system 100, it is possible to reduce the number of tapered slots 108. The minimum number of tapered slots 108 according to the invention is one tapered slot 108.

In an embodiment flexible sterile container 104 is sterilized prior to being employed in cryopreservation or cryoprocessing of biopharmaceutical materials according to the present invention, i.e. flexible sterile container 104 is pre-sterilized. If it is desirable to maintain sterility of the biopharmaceutical materials during processing, appropriate precautions must be observed in subsequent manipulation of pre-sterilized flexible sterile container 104.

Flexible sterile container 104 is comprised of a biocompatible polymeric material to promote relative compatibility with biopharmaceutical materials 110 and to avoid undesirable leaching of components from flexible sterile container 104 into biopharmaceutical materials 110. In the context of this application, biocompatible material characteristics involve benign interaction with biopharmaceutical material 110 such that the structure, activity and efficacy of biopharmaceutical materials 110 are not negatively impacted and any viable biopharmaceutical materials 110, such as cellular and tissue products, are not exposed to toxic effects. Suitable biocompatible polymeric materials within the scope of the present invention comprise ethylene-vinyl acetate copolymer, ethylene-vinyl alcohol copolymer, polytetrafluoroethylene, polyethylene, polyesters, polyamides, polypropylenes, polyvinylidenefluoride, polyurethanes, polyvinylchlorides, and mixtures or laminates that comprise the above.

Sterile flexible container 104 contains biopharmaceutical materials 110. In an embodiment, biopharmaceutical materials 110 may comprise protein solutions, protein formulations, amino acid solutions, amino acid formulations, peptide solutions, peptide formulations, DNA solutions, DNA formulations, RNA solutions, RNA formulations, nucleic acid solutions, nucleic acid formulations, biological cell suspensions, biological cell fragment suspensions (including cell organelles, nuclei, inclusion bodies, membrane proteins, and/or membranes), tissue fragments suspensions, cell aggregates suspensions, biological tissues in solution, organs in solution, embryos in solution, cell growth media, serum, biologicals, blood products, preservation solutions, fermentation broths, and cell culture fluids with and without cells, and mixtures of the above.

Flexible sterile container 104 may vary in size and may accommodate a wide range of biopharmaceutical material volumes. As flexible sterile container 104 varies in size, it may be necessary to vary the size of tapered slot 108 so as to accommodate flexible sterile container 104. One the other hand, tapered slot 108 may accommodate flexible sterile containers 104 of different heights, and thus different volumes. The size of tapered slot 108 may be determined using conventional techniques. In a preferred embodiment, flexible sterile container 104 has a volumetric capacity in a range from approximately 20 milliliters to approximately 1000 liters, and more preferably in a range from approximately 500 milliliters to approximately 100 liters. In alternative preferred embodiments, flexible sterile container 104 has a volumetric capacity in a range from approximately 100 milliliters to approximately 500 milliliters, from approximately 1 liter to approximately 20 liters, or from approximately 0.5 milliliters to approximately 50 liters.

Biopharmaceutical materials 110 comprise solid mass 124, dendritic freezing front 126 and dendrites 128. Temperature sensor port 130 is mechanically coupled to an upper surface of flexible sterile container 104 and protrudes inside flexible sterile container 104. In a preferred embodiment, temperature sensor port 130 serves to aseptically locate temperature sensor 116 within biopharmaceutical materials 110, enabling the temperature of biopharmaceutical materials 110 at that point to be fed back to control system 112. Temperature sensor 116 may comprise a thermocouple, a thermistor, an RTD, or other conventional temperature sensing devices suitable for use in a cryogenic environment. In an alternative preferred embodiment, temperature sensor 116 is disposed outside flexible sterile container 104 and comprises a temperature remote-sensing device. In such a preferred embodiment, temperature sensor 116 preferably comprises an infrared temperature sensing device.

In alternative embodiments, supplemental ports, preferably supplemental aseptic ports, are mechanically coupled to the upper surface of flexible container 104 in addition to aseptic port 106, similarly protruding and extending into flexible sterile container 104. In alternative embodiments, supplemental aseptic ports mechanically coupled to the upper surface of flexible sterile container 104 comprise temperature sensors 116 that measure the internal temperature of biopharmaceutical materials 110 at additional points. In alternative embodiments, supplemental remote-sensing temperature sensors may be disposed outside flexible sterile container 104 to measure the internal temperature of biopharmaceutical materials 110 at additional points.

In an embodiment, the supplemental aseptic ports include an aseptic port that permits introduction of biopharmaceutical materials 110 into flexible sterile container 104 or withdrawal of biopharmaceutical materials 110 from flexible sterile container 104. In alternative embodiments, the supplemental ports may include one or more of each of the following types of ports: filling ports, emptying ports, vent ports, sampling ports, additional temperature measuring ports (in a preferred embodiment comprising a capped tip), spectroscopic or light-based probe tube ports (in a preferred embodiment comprising a tip capped with a clear or transparent lens to accommodate, e.g., a fiber optic spectroscopic probe, or an optical dendritic freezing front sensing probe), ultrasonic dendritic freezing front sensing probe ports, ports to accommodate electrical conductivity or pH electrodes, and others.

Flexible sterile container 104 exhibits structural flexibility. Structural flexibility means that walls of flexible sterile container 104 deform under the static head of biopharmaceutical materials inside of flexible sterile container 104. In alternative embodiments, flexible sterile container 104 ranges in shape and structural characteristics from a soft-walled container which can be folded, or while empty collapses by itself, through a stiffer design which has flexible walls and can be stored in collapsed shape, but might maintain some of its own shape when empty, to a semi-rigid type, which can maintain its shape when empty and deforms partly only when filled with product (i.e., it possesses sufficient flexibility to adapt to the cryocooling walls shape).

An advantage of flexible sterile container 104 is its characteristic of conforming to the shape of tapered slot 108. This characteristic is of significance in promoting thermal contact quality and repeatability between flexible sterile container 104 and tapered slot 108. The higher the quality and repeatability of the thermal contact between flexible sterile container 104 and tapered slot 108, the better the cryopreservation performance of biopharmaceutical material cryopreservation system 100. The dendritic freezing front velocity depends, among other factors, on heat flux which in turn depends upon the quality of the thermal contact. The thermal contact between the wall of flexible sterile container 104 and tapered slot 108 depends upon the amount of air, with its thermally insulating properties, that is present in any gap between the wall of flexible sterile container 104 and tapered slot 108. Accordingly, pressing the wall of flexible sterile container 104 against tapered slot 108 may serve to improve the quality and repeatability of thermal contact. Thermal contact quality and repeatability may be enhanced in a variety of ways, including imparting a slight internal pressure to flexible sterile container 104, for example through use of an inert gas blanket. Alternatively, a weight may be located on top of flexible sterile container 104, thus pressing the contents of flexible sterile container 104, including any biopharmaceutical materials 110, against the walls of flexible sterile container 104, and thereby enhancing thermal contact quality and repeatability. Thermal greases may also be used.

In an embodiment, flexible sterile container 104 may be folded for storage or transportation and unfolded prior to being used for cryopreservation or cryoprocessing according to the present invention. In a related embodiment, temperature sensor port 130 and any supplemental aseptic ports coupled to flexible sterile container 104 exhibit various degrees of flexibility to facilitate the folding and unfolding of flexible sterile container 104 and may be folded together with flexible sterile container 104.

In an embodiment, temperature sensor port 130 protrudes and extends into a substantially central area of flexible sterile container 104. An advantage of disposing temperature sensor port 130 in the substantially central area of flexible sterile container 104 is that the portion of biopharmaceutical materials 110 located in this area may be the last to freeze when the biopharmaceutical material cryopreservation system 100 is in operation, therefore maximizing the time available for temperature sensor 116 to measure the temperature of biopharmaceutical materials 110 in a liquid state.

In an alternative embodiment, temperature sensor port 130 is inflexible and is disposed in the substantially-central area of flexible sterile container 104. In this embodiment, flexible sterile container 104 may be folded longitudinally, along inflexible aseptic port 108 and any additional aseptic ports coupled to flexible sterile container 104.

Freezing system 102 comprises control system 112, cryorefrigeration system 114 and temperature sensor 116. Freezing system 102 is removably coupled to flexible sterile container 104 via tapered slot 108. Freezing system 102 is thermally coupled to biopharmaceutical materials 110 via flexible sterile container 104 and tapered slot 108. Control system 112 is coupled to temperature sensor 116 and to cryorefrigeration system 114. In an embodiment, control system 112 and cryorefrigeration system 114 are located outside cryocooling enclosure 106 and are coupled to it. In an alternative embodiment, cryocooling control system 112 may be disposed inside cryocooling enclosure 106, but outside flexible sterile container 104. In yet another embodiment, cryocooling control system 112 may be disposed inside temperature sensor port 130.

Cryorefrigeration system 114 comprises cryocoolant input flow 118 and cryocoolant output flow 120, both of which are coupled to cryocooling enclosure 106, thereby coupling cryorefrigeration system 114 with cryocooling enclosure 106. Cryocooling enclosure 106 comprises cryocoolant 122, which is thermally coupled to biopharmaceutical materials 110. Crycooling enclosure 106 is constructed so as to flow cryocoolant 122 in a series fashion past each flexible sterile container 104 through hoses 132. In another embodiment (not shown in FIG. 1), flow of cryocoolant 122 may be performed in a parallel fashion past flexible sterile container 104. In an embodiment, cryocoolant 122 may comprise air or other gases (particularly effective when used under forced flow conditions), liquid silicone heat transfer fluid, alcohol, freons, polyethylene glycol, freezing salty brines (e.g. $CaCl_2$ brines), or liquid nitrogen.

The elements of freezing system 102 are constructed so as to comprise a feedback loop. The feedback loop is constructed to control the velocity (i.e. growth rate) of dendritic freezing front 126, within biopharmaceutical materials 110, in a range from approximately 5 millimeters per hour to approximately 250 millimeters per hour based on feedback information from temperature sensor 116.

In operation, cryorefrigeration system 114 cools the internal volume of cryocooling enclosure 106 by removing heat from that volume. As cryorefrigeration system 114 removes heat from within cryocooling enclosure 106, the temperature inside cryocooling enclosure 106 but outside flexible sterile container 104 decreases. As a result, a temperature gradient develops between cryocoolant 122 volume outside flexible sterile container 104 but inside cryocooling enclosure 106 and the warmer volume of biopharmaceutical materials 110. As a result of this temperature gradient, and because flexible sterile container 104 permits heat to be exchanged across its surfaces, heat is removed from biopharmaceutical materials 110, thereby cryocooling biopharmaceutical materials 110. Consequently, cryorefrigeration system 114 indirectly cools biopharmaceutical materials 110.

Cryorefrigeration system 114 feeds cryocoolant 122 into cryocooling enclosure 106 through cryocoolant input flow 118. Cryorefrigeration system 114 recirculates cryocoolant 122 through cryocooling enclosure 106 by removing cryocoolant 122 through cryocoolant recirculator 120. In a preferred embodiment, when biopharmaceutical materials 110 are being cooled down, the temperature of cryocoolant 122 fed by cryorefrigeration system 114 into cryocooling enclosure 106 through cryocoolant input flow 118 is lower than the temperature of cryocoolant 122 removed through cryocoolant recirculator 120. Consequently, in this embodiment, cryorefrigeration system 114 processes cryocoolant 122 to decrease its temperature before feeding it back into cryocooling enclosure 106.

Cryorefrigeration system 114 can alter the rate and direction in which the temperature of biopharmaceutical materials 110 varies by either modifying the temperature differential between cryocoolant 122 fed into cryocooling enclosure 106 and cryocoolant 122 removed from cryocooling enclosure 106, or by altering the rate at which cryocoolant 122 is circulated through cryocooling enclosure 106. In a preferred embodiment, when biopharmaceutical materials 110 are being frozen, to increase the freezing rate of biopharmaceutical materials 110, cryorefrigeration system 114 increases the temperature differential between cryocoolant 122 fed into cryocooling enclosure 106 and biopharmaceutical materials 110 by further cooling down cryocoolant 122. In an alternative related preferred embodiment, cryorefrigeration system 114 achieves the same goal by maintaining the temperature differential between cryocoolant 122 fed into cryocooling enclosure 106 and cryocoolant 122 removed from cryocooling enclosure 106 unchanged, but instead increasing the rate at which it recirculates cryocoolant 122 through cryocooling enclosure 106 by increasing its flow rate through cryorefrigeration system 114.

In an embodiment, cryocoolant 122 flow rate is increased, and the outlet temperature of cryocoolant 122 is decreased. This arrangement serves to lower a mean temperature of cryocoolant 122 (with the mean being the mean of the inlet and outlet temperatures) and thus provides a higher driving force (mean temperature difference between the biopharmaceutical material 110 and the mean temperature (inlet-outlet) of cryocoolant 122) for freezing and increases the dendritic freezing front velocity. Higher cryocoolant flow rate also increases the heat transfer coefficient on the cryocoolant 122 side of tapered slot 108, thus increasing the heat flux withdrawn from biopharmaceutical material 110, further increasing the dendritic freezing front velocity.

In an alternative preferred embodiment, when biopharmaceutical materials 110 are being cooled down, to increase or decrease the freezing rate of biopharmaceutical materials 110, cryorefrigeration system 114 decreases the temperature differential between cryocoolant 122 fed into cryocooling enclosure 106 and cryocoolant 122 removed from cryocooling enclosure 106 by decreasing the amount by which it cools down cryocoolant 122. In an alternative related preferred embodiment, cryorefrigeration system 114 maintains the temperature differential between cryocoolant 122 fed into cryocooling enclosure 106 and cryocoolant 122 removed from cryocooling enclosure 106 unchanged, but decreases or increases the rate at which it recirculates cryocoolant 122 through cryocooling enclosure 106 by decreasing or increasing its speed through cryorefrigeration system 114.

In an embodiment, by varying the temperature of cryocoolant 122 or the rate at which cryocoolant 122 is recirculated through cryocooling enclosure 102, cryorefrigeration system 114 controls the rate of cryocooling/freezing or warming of biopharmaceutical materials 110. In this embodiment, temperature sensor 116 continuously monitors the temperature of biopharmaceutical materials 110 and transmits that information to control system 112. In an alternative embodiment, multiple temperature sensors are disposed within flexible sterile container 104 to measure the temperature of biopharmaceutical materials 110 at multiple locations. Cryorefrigeration system 114 measures the temperature of cryocoolant 122 as it enters and exits cryocooling enclosure 106 and transmits that information to control system 112. Control system 112 then directs cryorefrigeration system 114 to appropriately alter the flow rate of cryocoolant 122.

In an embodiment, as cryocoolant 122 removes heat from flexible sterile container 104, the temperature of biopharmaceutical materials 110 decreases. Eventually, if this process continues for a sufficiently long period of time, a phase transition may commence within biopharmaceutical materials 110 in the proximity of the external surfaces of flexible sterile container 104. As the temperature of biopharmaceutical materials 110 continues to decrease, biopharmaceutical materials 110 freeze and solidify in the proximity of the surfaces of flexible sterile container 104, thereby producing solid mass 124, with dendritic freezing front 126 gradually moving into the bulk volume of pharmaceutical material 110.

An important distinction between the present invention and conventional freezing techniques is that the present invention comprises a feedback loop that comprises the temperature of biopharmaceutical materials 110, rather than only the temperature of cryocoolant 122. For instance, conventional cabinet or chest freezers are so constructed as to have a feedback loop that controls the temperature of the air inside the cabinet or chest freezer that serves as the cryocoolant. In this regard, little or no control is possible of the freezing fronts within any containers located in the cabinet or chest freezer. Variables such as location of the container within the cabinet or chest freezer, number of containers within the cabinet or chest freezer, geometry of the container, wall thickness of the container, material of construction of the container, and so on combine to make practical control of the freezing front within the container difficult or impossible.

In contrast, the present invention controls the rate of dendritic freezing front 126 velocity within biopharmaceutical materials 110 through fedback temperature information regarding biopharmaceutical materials 110 from temperature sensor 116. This feedback loop permits more precise control of heat removal from biopharmaceutical materials 110, and facilitates control of the dendritic freezing front 126 velocity to within the recited ranges. Variables such as location within cryocooling enclosure 106, wall thickness of flexible sterile container 104, thermal resistance between flexible sterile container 104, and tapered slot 108, etc., are automatically taken into account through the feedback loop. Absent the feedback loop that comprises temperature of the biopharmaceutical materials 110, more precise control of the dendritic freezing front velocity would be practically difficult to accomplish.

Dendritic freezing front 126 separates biopharmaceutical materials 110 present as solid mass 124 from the liquid form of biopharmaceutical materials 110, thereby producing a solid-liquid interface in which dendrites 128 are forming. As heat removal from biopharmaceutical materials 110 continues, dendritic freezing front 126 advances away from the inner surface of flexible sterile container 104, as additional liquid biopharmaceutical materials 110 freeze into solid mass 124. In an embodiment of the present invention, the dendritic freezing front velocity is the velocity with which dendritic freezing front 126 advances.

In an embodiment, the rate at which heat is removed (i.e. the heat flux) from biopharmaceutical materials 110 determines the velocity of dendritic freezing front 126. Since the temperature gradient between biopharmaceutical materials 110 and cryocoolant 122 is correlated with the rate at which heat is removed from biopharmaceutical materials 110, the velocity of dendritic freezing front 126 can be controlled by controlling the temperature of cryocoolant 122.

In a preferred embodiment, heat is removed from biopharmaceutical materials 110 at a rate that promotes a substantially uniform advance of dendritic freezing front 126 within substantially all volume of biopharmaceutical materials 110 or a substantially constant velocity of dendritic freezing front 128. Maintenance of a substantially constant velocity of dendritic freezing front 126 within flexible sterile container 104 according to an embodiment of this invention is desirable because it provides substantially steady-state conditions for undisturbed dendritic ice crystal growth, independently from the distance to the cooled heat transfer surface within the freezing volume.

Figure 2:
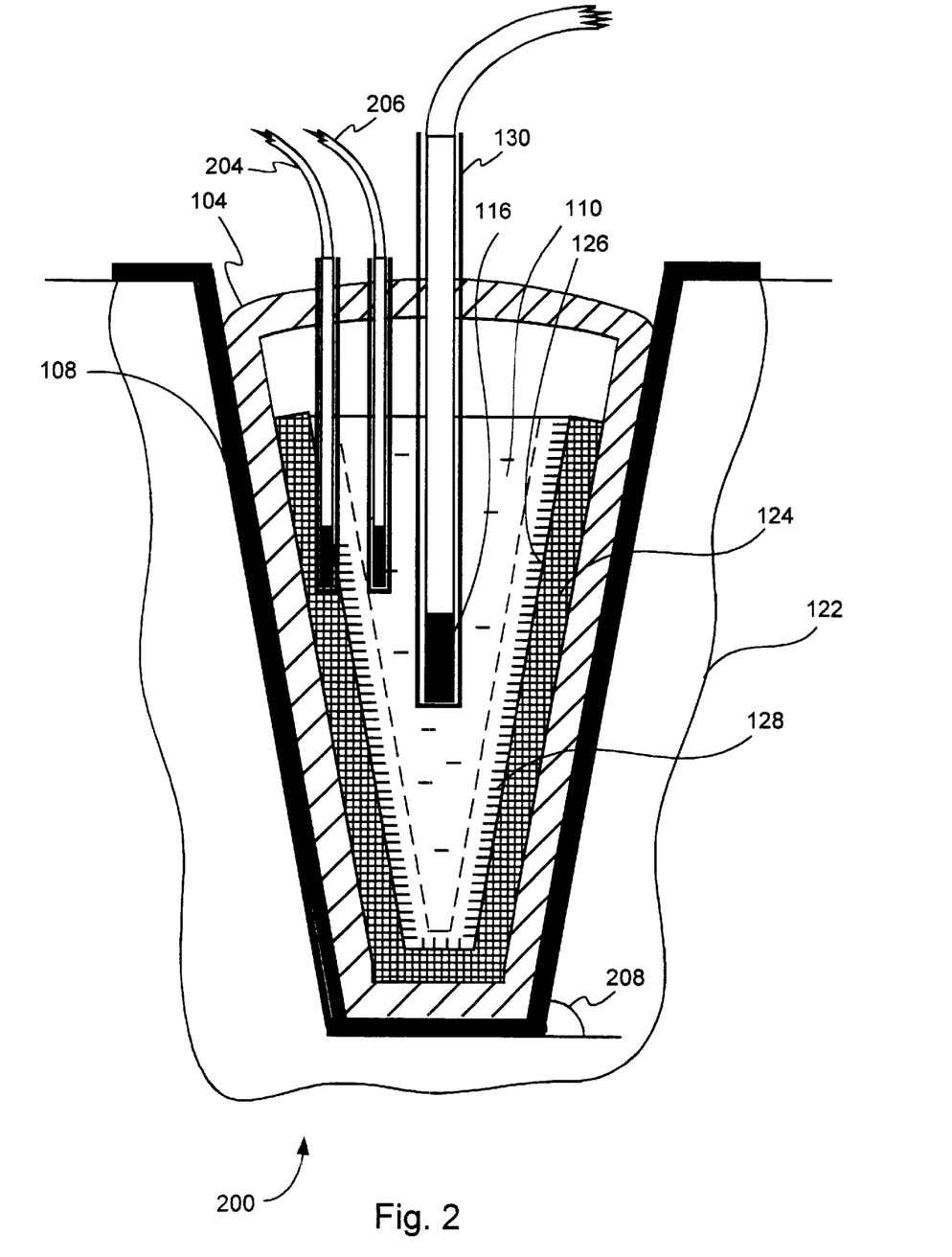
FIG. 2 shows another embodiment of a biopharmaceutical material cryopreservation system according to the present invention.

FIG. 2 shows a portion of a biopharmaceutical material cryopreservation system according to the present invention. Biopharmaceutical material cryopreservation system 200 comprises flexible sterile container 104, tapered slot 108, biopharmaceutical materials 110, temperature sensor 116, cryocoolant 122, solid mass 124, dendritic freezing front 126, dendrites 128, temperature sensor port 130, second temperature sensor 204, third temperature sensor 206, and taper angle 208.

The arrangement and operation of biopharmaceutical material cryopreservation system 200 is substantially similar to that of Biopharmaceutical material cryopreservation system 100, except that second temperature sensor 204, and third temperature sensor 206 are present. Second temperature sensor 204 and third temperature sensor 206 serve to provide information about the temperature gradient that exists perpendicular to the wall.

Tapered slot 108 in FIG. 2 possesses a taper angle 208. Taper angle 208 may vary between 1 to 89 degrees, more preferably between about 75 to about 88 degrees. Taper angle 208 may be fixed or, in certain embodiments, may be adjustable. The taper angle may be adjusted for a variety of reasons. Taper angle selection depends upon the composition and concentration of the biopharmaceutical material. For example, smaller taper angles may be used for higher biopharmaceutical material concentrations, while larger taper angles may be used for lower biopharmaceutical material concentrations. Conventional mechanical mechanisms for adjusting the position of the side walls of tapered slot 108 may used in the practice of this invention, including positioning screws or positioning motors.

Further, the walls of tapered slot 108 may have a complex shape. Although a straight wall is shown in FIG. 2, the walls of tapered slot 108 according to the invention may be curved or have multiple segments or curves. For example, the side cooling walls may be flat or concave/convex to induce specific freezing patterns. In the embodiments where multiple segments or curves are present, the segments may have the same angle versus vertical axis, or they may have different angles (for example, one plate being at 75 deg and another at 80 deg). Also, the side cooling walls of tapered slot 108 may be angled differently from one another as a whole, creating an asymmetric tapered slot.

In another embodiment, the entire tapered slot 108 could be angled with respect to the vertical. In this embodiment, one wall of the tapered slot 108 would freeze the "bottom" of flexible sterile container 104, and the other would freeze the top. The top wall needs to be pressed against flexible sterile container 104 and flexible sterile container 104 has to have a pocket on its upper surface to accommodate a gas pocket (e.g. to have a head space).

Tapered slot 108 may plays multiple roles in freezing (and thawing) of biopharmaceutical products 110 in flexible sterile container 104. It primarily serves for heat removal during freezing and heat delivery during thawing. Tapered slot 108 facilitates stress-reducing controlled freezing by allowing a free product expansion upwards during freezing. This is accomplished by the taper of tapered slot 108. As biopharmaceutical product 110 freezes, the liquid aqueous phase will expand, by approximately 9–10% to reach the solid state. In the absence of tapered slot 108, pockets of liquid biopharmaceutical materials 110 may form initially as dendritic freezing fronts 126 approach one another. These pockets of liquid surrounded by solid mass 124 and/or the walls of sterile flexible container 104 may form due to:the shape and geometry of flexible sterile container 104, local heat gains through the wall of flexible sterile container 104 (uncooled, or unsinsulated parts of the container wall, sticking out heat sinks (like valves, nozzles, etc.)), complex shape of the solid-liquid interfaces, surface freezing (if the gas in the head space is cooled), heat-conducting elements inserted into a container (like sensor housings).

As these liquid pocket subsequently freeze, the liquid pockets expand, thus increasing stress on the solid mass 124 surrounding the liquid pocket. This stress can cause multiple effects detrimental to biopharmaceutical materials 110: biological cells can be ruptured, proteins may unfold, the solubility of gases and of solutes change (may lead to precipitation later), as well as changing structure of ice crystals under pressure. These effects may negatively affect biopharmaceutical materials 110 by the pressure alone, or may change the structure of solid mass 124 beyond the intended controlled dendritic structure.

In addition, such stress can lead to the situation when the external (surrounding the liquid pocket) solid mass 124 cannot bear the stress anymore and cracks randomly (such randomness can be anticipated due to uncontrolled nature of the liquid pocket formation). The 9% volume change can cause serious cracked solid mass 124 displacements. The stress buildup and cracking of solid mass 124 may cause damage of biopharmaceutical materials in the already correctly frozen solid mass 124, by damaging internal microstructures (cracking ice dendrites or shearing glassy states with biopharmaceutical material 110 embedded in them).

Random cracking of the solid mass 124 may also project forces on the walls of flexible sterile container 104. The stress buildup and cracking may cause the parts of solid mass 124 to displace and damage the wall of flexible sterile container 104, depending how the cracks progress and how the parts of the frozen material displace. Damage to the walls of flexible sterile container 104 may result in leakage and loss, or contamination or loss of sterility of biopharmaceutical material(s) 110.

The action of the taper of tapered slot 108 during freezing is to promote bottom-up freezing. In this situation, dendritic freezing fronts 126 approach one another first at the bottom of tapered slot 108. As dendritic freezing fronts 126 continue to approach one another, any liquid biopharmaceutical materials 110 are driven upwards into a headspace present in flexible sterile container 104, and are generally not trapped as liquid pockets between dendritic freezing fronts 126 or elsewhere within flexible sterile container 104. In this way, tapered slot 108 reduces the number of liquid pockets formed, therefore providing stress-reducing freezing. Stress-reducing freezing may therefore be considered to be freezing wherein the number of liquid pockets formed, leading to subsequent expansion and stress, is zero for large liquid pockets (i.e. pockets above 10% of the freezing volume), and less than 5 for small liquid pockets (i.e. liquid pockets that are 10% or less of the freezing volume).

To promote bottom-up freezing, a temperature gradient having a vertical component can be developed in the walls of tapered slot 108. This can be accomplished in a variety of ways. For instance, cryocooling fluid 122 could be introduced at the bottom of cryocooling enclosure 106 and leave at the top. Other embodiments include manipulation of heat transfer coefficients; with higher values at the bottom of the walls of tapered slot 108 and lower values at the top. This provides for different heat fluxes at the top and the bottom of tapered slot 108 and the resulting heat flux gradient induces bottom-up freezing, i.e. stress-reducing freezing.

Tapered slot 108 also supports flexible sterile container 104, providing a template for the final shape of flexible sterile container 104 that it assumes after it is filled with product. The tapered geometry shapes flexible sterile container 104 to the slot dimensions which are important for freezing. As discussed more fully above, tapered slot 108 also provides a good thermal contact due to the hydrostatic pressure distribution from the walls of flexible sterile container 104 walls onto the walls of tapered slot 108.

Temperature monitoring inside flexible sterile container 104 may be performed in the center of flexible sterile container 104, with temperature sensor 116 being placed along the centerline of flexible sterile container 104, In this embodiment, temperature sensor 116 serves, among other functions, to indicate the end of freezing (disappearance of the liquid phase). In such an embodiment, temperature sensor 116 thus provides information about dendritic front growth rate, and functions as a part of the feedback loop.

In another embodiment, temperatures sensors may be placed to monitor the temperature gradient within biopharmaceutical material 110, with temperature sensors, for example second temperature sensor 204 and third temperature sensor 206 being placed off the centerline (e.g. between the centerline and the wall of flexible sterile container 104). A direct gradient reading can be performed with a multiple point temperature sensor or using multiple temperature sensors, as shown in FIG. 2.

In an embodiment, multiple readings may be as follows:third temperature sensor 206 located near the wall of flexible sterile container 104, second temperature sensor 204 at a certain distance from the wall of flexible sterile container 104, and temperature sensor 116 at the centerline. Second temperature sensor 204 and third temperature sensor 206 serve to monitor a temperature gradient in solid mass 124, whereas the centerline sensor will indicate the end of freezing. The measured temperature gradient in solid mass 124 is related to the freezing front velocity and thus can be used by the control system. Since the dendritic growth is controlled by the heat flux/front velocity, thus the measured temperature gradient can be used to control the dendritic growth.

Figures 3, 3A, 3B:
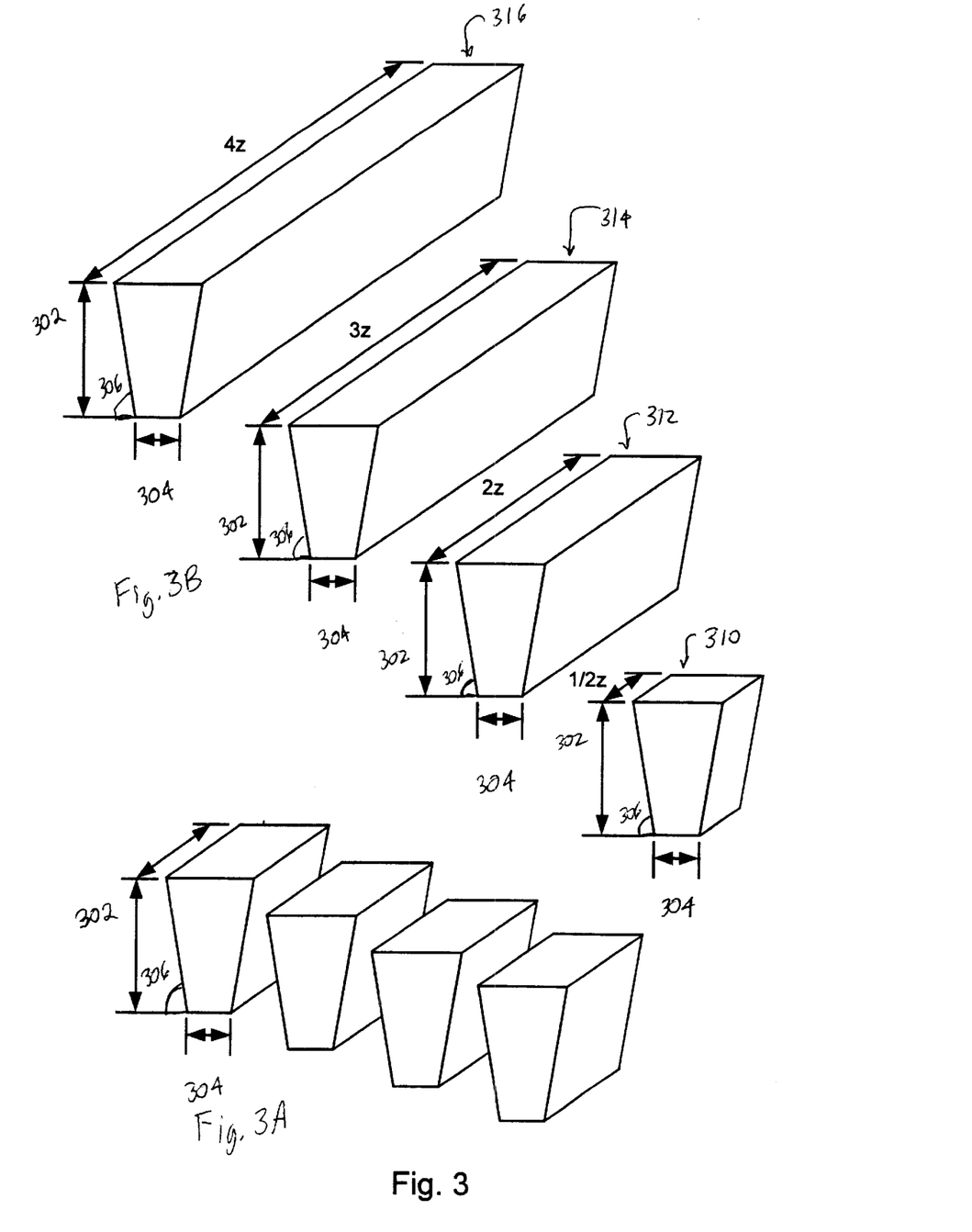
FIGS. 3A–B show linear scaling of the biopharmaceutical material cryopreservation system according to the present invention.

FIGS. 3A–B show several views of tapered slot biopharmaceutical material cryopreservation system 300.

FIG. 3A shows that, while the height 302, slab length 304, and taper angle 306 may be kept constant, linear scale up can be achieved by increasing the number of tapered slots. This concept has also been discussed above.

FIG. 3B exhibits another manner of achieving linear scale up. Again, height 302, slab length 304, and taper angle 306 may be kept constant. In this embodiment, once the optimum dimensions and freezing front velocity are defined, the "z" dimension can be increased or decreased to linearly increase or decrease the freezing volume of the system. For example, tapered slot 310 having a z dimension of ½z has one-fourth of the volume of tapered slot 312, and ⅛$^{th}$ the volume of tapered slot 316, which has a z dimension of 4 z. The volume scales linearly, as for example seen in tapered slot 314, wherein tapered slot 314 has a z dimension of 3, compared to tapered slot 316's z dimension of 4. Accordingly, tapered slot 314 has twenty-five percent less volume than tapered slot 316.

In use, the heat removal capacity of the cooling system may be changed in proportion to the length of the vessel, while maintaining the same cooling surface temperature. To the extent that different length containers may be made, e.g. using flexible, polymeric materials, processes of different scale may be designed based on cooling systems with a common aspect ratio corresponding to the optimum cross-sectional size and shape of the container. In this way, small volumes as well as large volumes will have similar thermal histories and hence the quality of the product may remain constant regardless of the scale.

In another embodiment, multiple flexible sterile containers of different volumes can be used to stored, freeze and thaw the production lot, providing additional flexibility. For example, a sampling bag of the same cross-sectional geometry but containing only a fraction of the volume can be frozen close to the process bag. Once frozen, the sample bag may be removed, and the contents analyzed. A sample frozen and thawed in the sampling bag will have identical thermal history to the product processed in the corresponding large-scale bag.

Additional flexibility is also provided by the possibility to freeze in a given cooling plate assembly, a bag of smaller z length than the one allowed by the plate dimensions. In this situation, the bag can be placed between two insulation pads in the center of the plates to minimize end effects.

EXAMPLE 1

The following example illustrates a scale-up using a slab approach. The slab length is constant, 12 cm—as well as the height, 40 cm. A 40-scale volume increase is achieved by freezing in a parallel arrangement 10 cm or 42 cm long containers. The freezing time and freezing rate are maintained at constant values.

TABLE 1

| Scale-up factor | 1 | 4 | 20 | 40 |
|---|---|---|---|---|
| Volume (L) | 5 | 20 | 100 | 200 |
| Container length (cm) | 10 | 42 | 20 | 417 |
| Nbr of 42 cm length containers | 0.25 | 1 | 5 | 10 |

It will be apparent to those skilled in the art that various modifications and variations can be made in the cryopreservation system components, systems and methods of the present invention without departing from the spirit or scope of the invention. Thus, it is intended that the present invention covers the modifications and variations of this invention provided they come within the scope of the appended claims and their equivalents.

What is claimed is:

1. A biopharmaceutical material cryopreservation system, comprising:

a flexible sterile container comprising a biocompatible polymeric material, and the flexible sterile container containing biopharmaceuticals materials, and;

a freezing system removably coupled to the flexible sterile container via a tapered slot and the freezing system thermally coupled to the biopharmaceutical materials via the flexible sterile container and the tapered slot;

wherein the freezing system comprises a feedback loop constructed to control a dendritic freezing front velocity, within the biopharmaceutical materials, in a range from approximately 5 millimeters per hour to approximately 250 millimeters per hour based on feedback information from the temperature sensor.

2. The biopharmaceutical material cryopreservation system of claim 1, wherein the biocompatible polymeric material comprises ethylene-vinyl acetate copolymer, ethylene-vinyl alcohol copolymer, polytetrafluoroethylene, polyethylene, polyesters, polyamides, polypropylenes, polyvinylidenefluoride, polyurethanes, polyvinylchlorides, and mixtures or laminates that comprise the above.

3. The biopharmaceutical material cryopreservation system of claim 1, wherein the flexible sterile container possesses a volumetric capacity in a range from approximately 20 milliliters to approximately 1000 liters.

4. The biopharmaceutical material cryopreservation system of claim 1, wherein the flexible sterile container possesses a volumetric capacity in a range from approximately 500 milliliters to approximately 100 liters.

5. The biopharmaceutical material cryopreservation system of claim 1, wherein the flexible sterile container possesses a volumetric capacity in a range from approximately 100 milliliters to approximately 500 milliliters.

6. The biopharmaceutical material cryopreservation system of claim 1, wherein the flexible sterile container possesses a volumetric capacity in a range from approximately 1 liter to approximately 20 liters.

7. The biopharmaceutical material cryopreservation system of claim 1, wherein the flexible sterile container possesses a volumetric capacity in a range from approximately 0.5 milliliters to approximately 50 liters.

8. The biopharmaceutical material cryopreservation system of claim 1, wherein the freezing system comprises a feedback loop constructed to control a dendritic freezing front velocity, within the biopharmaceutical materials, in a range from approximately 8 millimeters per hour to approximately 180 millimeters per hour based on feedback information from the temperature sensor.

9. The biopharmaceutical material cryopreservation system of claim 1, wherein the freezing system comprises a feedback loop constructed to control a dendritic freezing front velocity, within the biopharmaceutical materials, in a range from approximately 10 millimeters per hour to approximately 125 millimeters per hour based on feedback information from the temperature sensor.

10. The biopharmaceutical material cryopreservation system of claim 1, wherein the biopharmaceutical materials comprise protein solutions; protein formulations; amino acid solutions; amino acid formulations; peptide solutions; peptide formulations; DNA solutions; DNA formulations; RNA solutions; RNA formulations; nucleic acid solutions; nucleic acid formulations; biological cell suspensions; biological cell fragment suspensions including cell organelles, nuclei, inclusion bodies, membrane proteins, and/or membranes; tissue fragments suspensions; cell aggregates suspensions; biological tissues in solution; organs in solution; embryos in solution; cell growth media; serum; biologicals; blood products; preservation solutions; fermentation broths; and cell culture fluids with and without cells; and mixtures of the above.

11. The biopharmaceutical material cryopreservation system of claim 1, wherein a taper angle ranges from about 75 to about 88 degrees.

12. A method for cryopreservation of biopharmaceutical materials, comprising:

provrding a flexible sterile container comprising a biocompatible polymeric material, and the flexible sterile container containing biopharmaceuticals materials;

thermally coupling a freezing system to the biopharmaceutical materials via the flexible sterile container, and the freezing system comprising (i) a temperature sensor that monitors a temperature of the biopharmaceutical materials, and (ii) a feedback loop constructed to control a dendritic freezing front velocity; and controlling the dendritic freezing front velocity, within the biopharmaceutical materials, in a range from approximately 5 millimeters per hour to approximately 250 millimeters per hour based on feedback information from the temperature sensor.

13. The method of claim 12, wherein the biocompatible polymeric material comprises ethylene-vinyl acetate copolymer, ethylene-vinyl alcohol copolymer, polytetrafluoroethylene, polyethylene, polyesters, polyamides, polypropylenes, polyvinylidenefluoride, polyurethanes, poly-vinylchlorides, and mixtures or laminates that comprise the above.

14. The method of claim 12, wherein the flexible sterile container possesses a volumetric capacity in a range from approximately 20 milliliters to approximately 1000 liters.

15. The method of claim 12, wherein the flexible sterile container possesses a volumetric capacity in a range from approximately 500 milliliters to approximately 100 liters.

16. The method of claim 12, wherein the flexible sterile container possesses a volumetric capacity in a range from approximately 100 milliliters to approximately 500 milliliters.

17. The method of claim 12, wherein the flexible sterile container possesses a volumetric capacity in a range from approximately 1 liter to approximately 20 liters.

18. The method of claim 12, wherein the flexible sterile container possesses a volumetric capacity in a range from approximately 0.5 milliliters to approximately 50 liters.

19. The method of claim 12, wherein the dendritic freezing front velocity is controlled in a range from approximately 8 millimeters per hour to approximately 180 millimeters per hour based on feedback information from the temperature sensor.

20. The method of claim 12, wherein the dendritic freezing front velocity is controlled in a range from approximately 10 millimeters per hour to approximately 125 millimeters per hour based on feedback information from the temperature sensor.

21. The method of claim 12, wherein the biopharmaceutical materials comprise protein solutions; protein formulations; amino acid solutions; amino acid formulations; peptide solutions; peptide formulations; DNA solutions; DNA formulations; RNA solutions; RNA formulations; nucleic acid solutions; nucleic acid formulations; biological cell suspensions; biological cell fragment suspensions including cell organelles, nuclei, inclusion bodies, membrane proteins, and/or membranes; tissue fragments suspensions; cell aggregates suspensions; biological tissues in solution; organs in solution; embryos in solution; cell growth media; serum; biologicals; blood products; preservation solutions; fermentation broths; and cell culture fluids with and without cells; and mixtures of the above.

22. The method of claim 12, wherein a taper angle ranges from about 75 to about 88 degrees.

23. A biopharmaceutical material cryopreservation system, comprising flexible sterile container means for counting biopharmaceutical products, and the flexible sterile container means comprising a biocompatible polymeric material, and the flexible sterile container containing biopharmaceuticals materials, and;

freezing means for freezing the biopharmaceutical materials, and the freezing means thermally coupled to the biopharmaceutical materials via the flexible sterile container, and the freezing means comprising a temperature sensor that monitors a temperature of the biopharmaceutical materials wherein the freezing means comprises a feedback loop constructed to control a dendritic freezing front velocity, within the biopharmaceutical materials, in a range from approximately 5 millimeters per hour to approximately 250 millimeters per hour based on feedback information from the temperature sensor.

24. The biopharmaceutical material cryopreservation system of claim 23, wherein the biocompatible polymeric material comprises ethylene-vinyl acetate copolymer, ethylene-vinyl alcohol copolymer, polytetrafluoroethylene, polyethylene, polyesters, polyamides, polypropylenes, polyvinylidenefluoride, polyurethanes, polyvinylchlorides, and mixtures or laminates that comprise the above.

25. The biopharmaceutical material cryopreservation system of claim 23, wherein the freezing system comprises a feedback loop constructed to control a dendritic freezing front velocity, within the biopharmaceutical materials, in a range from approximately 8 millimeters per hour to approximately 180 millimeters per hour based on feedback information from the temperature sensor.

26. The biopharmaceutical material cryopreservation system of claim 23, wherein the freezing system comprises a feedback loop constructed to control a dendritic freezing front velocity, within the biopharmaceutical materials, in a range from approximately 10 millimeters per hour to approximately 125 millimeters per hour based on feedback information from the temperature sensor.

27. The biopharmaceutical material cryopreservation system of claim 23, wherein the biopharmaceutical materials comprise protein solutions; protein formulations; amino acid solutions; amino acid formulations; peptide solutions; peptide formulations; DNA solutions; DNA formulations; RNA solutions; RNA formulations; nucleic acid solutions; nucleic acid formulations; biological cell suspensions; biological cell fragment suspensions including cell organelles, nuclei, inclusion bodies, and/or membranes; tissue fragments suspensions; cell aggregates suspensions; biological tissues in solution; organs in solution; embryos in solution; cell growth media; serum; biologicals; blood products; preservation solutions; fermentation broths; and cell culture fluids with and without cells; and mixtures of the above.

28. A method of linearly scaling a process for cryopreserving a biopharmaceutical material comprising:

providing the biopharmaceutical material cryopreservation system of claim 1, wherein the biopharmaceutical material cryopreservation system possesses a first volume defined by a slab length, height, taper angle, and a first z dimension;

determining a second volume;

determining a second z dimension based on the values of the second volume, the slab length, the height, and the taper angle; and providing the biopharmaceutical material cryopreservation system, wherein the biopharmaceutical material cryopreservation system possesses the second volume defined by the slab length, the height, the taper angle, and the second z dimension.

* * * * *

UNITED STATES PATENT AND TRADEMARK OFFICE
CERTIFICATE OF CORRECTION

PATENT NO.    : 6,453,683 B1
DATED         : September 24, 2002
INVENTOR(S)   : Richard Wisniewski and Eric Lee It is certified that error appears in the above-identified patent and that said Letters Patent is hereby corrected as shown below:

Column 16,
Line 10, amend:
"back information from the temperature sensor." to read
-- back information from a temperature sensor. --

Signed and Sealed this

Sixteenth Day of December, 2003

JAMES E. ROGAN
*Director of the United States Patent and Trademark Office*